US00PP15495P2

(12) United States Plant Patent
Hanes

(10) Patent No.: US PP15,495 P2
(45) Date of Patent: Jan. 25, 2005

(54) ***GERANIUM* PLANT NAMED 'CLIPS ROSSPLA'**

(50) Latin Name: *Pelargonium×hortorum*
Varietal Denomination: Clips Rosspla

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,372

(22) Filed: Apr. 5, 2004

(51) Int. Cl.[7] ..... A01H 5/00
(52) U.S. Cl. ..... Plt./324
(58) Field of Search ..... Plt./324

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Geranium* plant named 'Clips Rosspla', characterized by its upright, outwardly spreading and rounded growth habit; freely basal branching habit; dark green-colored leaves; freely flowering habit with many flower umbels per plant; and flower umbels with numerous red and red purple bi-colored single flowers.

1 Drawing Sheet

Botanical classification/cultivar designation: *Pelargonium×hortorum* cultivar Clips Rosspla.

BACKGROUND OF THE INVENTION

The present invention relates to a new and distinct cultivar of *Geranium* plant, botanically known as *Pelargonium× hortorum*, commercially known as a Zonal *Geranium*, and hereinafter referred to by the name 'Clips Rosspla'.

The new *Geranium* is a product of a planned breeding program conducted by the Inventor in Gilroy, Calif. The objective of the breeding program is to develop new Zonal *Geranium* cultivars with good basal branching, freely flowering habit and attractive flower and foliage coloration.

The new *Geranium* originated from a cross-pollination made by the Inventor in April, 2000 of a proprietary *Pelargonium×hortorum* selection identified as code number 6593-1, not patented, as the female, or seed, parent with a proprietary *Pelargonium×hortorum* selection identified as code number 7798-1, not patented, as the male, or pollen, parent. The cultivar Clips Rosspla was discovered and selected by the Inventor as a flowering plant within the progeny from this cross-pollination in a controlled environment in Gilroy, Calif. in September, 2000.

Asexual reproduction of the new cultivar by terminal cuttings at Gilroy, Calif., since September, 2000 has shown that the unique features of this new *Geranium* are stable and reproduced true to type in successive generations of asexual reproduction.

SUMMARY OF THE INVENTION

The following traits have been repeatedly observed and are determined to be the unique characteristics of 'Clips Rosspla'. These characteristics in combination distinguish 'Clips Rosspla' as a new and distinct *Geranium* cultivar:

1. Upright, outwardly spreading and rounded growth habit.
2. Freely basal branching habit.
3. Dark green-colored leaves.
4. Freely flowering habit with many large flower umbels per plant.

5. Flower umbels with numerous red and red purple bi-colored single flowers.

In side-by-side comparisons conducted in Gilroy, Calif., plants of the new *Geranium* differed from plants of the female parent selection in the following characteristics:

1. Plants of the new *Geranium* were more vigorous than plants of the female parent selection.
2. Plants of the new *Geranium* and the female parent selection differed in flower color as plants of the female parent had violet-colored flowers.

In side-by-side comparisons conducted in Gilroy, Calif., plants of the new *Geranium* differed from plants of the male parent selection in the following characteristics:

1. Plants of the new *Geranium* had darker green-colored leaves than plants of the male parent selection.
2. Plants of the new *Geranium* and the male parent selection differed in flower coloration as plants of the male parent selection had red-colored flowers.

The new *Geranium* can be compared to the cultivar, Americana Red Splash, disclosed in U.S. Plant Pat. No. 9,306. However, in side-by-side comparisons conducted in Gilroy, Calif., plants of the new *Geranium* differed from plants of the cultivar Americana Red Splash in the following characteristics:

1. Plants of the new *Geranium* were more vigorous than plants of the cultivar Americana Rose Splash.
2. Plants of the new *Geranium* had darker green-colored leaves than plants of the cultivar Americana Red Splash.
3. Flowers of plants of the new *Geranium* and the cultivar Americana Red Splash differed in flower color as plants of the cultivar Americana Red Splash had dark pink and red purple bi-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Clips Rosspla'.

The photograph at the bottom of the sheet is a close-up view of typical flower umbels and leaves of 'Clips Rosspla'.

Flower and foliage colors in the photographs may differ slightly from the color values cited in the detailed botanical description which accurately describe the colors of the new *Geranium.*

DETAILED BOTANICAL DESCRIPTION

Plants of the cultivar Clips Rosspla have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a fiberglass-covered greenhouse during the late spring with day temperatures about 27 to 29° C., night temperatures about 16 to 18° C. and light levels about 2,000 foot-candles. Plants used for the photographs and description were about six months from planting rooted cuttings. In the following description, color references are made to The Royal Horticultural Society Colour Chart, 1995 Edition, except where general terms of ordinary dictionary significance are used.

Botanical classification: *Pelargonium×hortorum* cultivar Clips Rosspla.

Parentage:

*Female parent.*—Proprietary *Pelargonium×hortorum* selection identified as code number 6593-1, not patented.

*Male parent.*—Proprietary *Pelargonium×hortorum* selection identified as code number 7798-1, not patented.

Propagation:

*Type cutting.*—Terminal cuttings.

*Time to initiate roots.*—About 12 to 14 days at 24° C.

*Time to develop roots.*—About four weeks at 18 to 24° C.

*Root description.*—Fibrous, fine; white in color.

*Rooting habit.*—Freely branching.

Plant description:

*General appearance.*—Upright, outwardly spreading and rounded growth habit.

*Growth and branching habit.*—Vigorous and very freely basal branching with about 12 lateral branches. Pinching, that is, removal of terminal apices, is typically not required.

*Plant height to top of foliage.*—About 30 cm.

*Plant height to top of flower umbels.*—About 39 cm.

*Plant width.*—About 52 cm.

*Lateral branches.*—Length: About 24 cm. Diameter: About 1.1 cm. Internode length: About 2.5 mm. Texture: Pubescent. Color: 144B.

*Foliage description.*—Arrangement: Alternate, simple. Length: About 6.5 cm. Width: About 9.8 cm. Shape: Reniform with slight rounded lobes. Apex: Rounded. Base: Cordate. Margin: Crenate and serrate. Venation: Palmate. Texture, upper and lower surfaces: Velvety; pubescent; somewhat leathery. Color: Developing foliage, upper surface: 147A. Developing foliage, lower surfaced: 147B. Fully developed foliage, upper surface: Darker than 147A. Fully developed foliage, lower surface: Darker than 147B. Venation, upper surface: 147B. Venation, lower surface: 147C. Petiole: Length: About 10.5 cm. Diameter: About 3 mm. Texture, upper and lower surfaces: Pubescent. Color, upper and lower surfaces: 146B.

Flower description:

*Flower arrangement and type.*—Single rounded flowers arranged in hemispherical umbels arising from apical leaf axils. Umbels displayed above the foliage. At full flowering, usually about 17 open and developing umbels per plant. Flowers not persistent; umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about one week on the plant.

*Umbels.*—Height: About 6.5 cm. Diameter: About 12 cm. Number of flowers and flower buds per umbel: Freely flowering, about 38. Flower diameter: About 4 cm. Flower depth (height): About 2.5 cm.

*Flower buds.*—Length: About 2 cm. Diameter: About 8 mm. Shape: Ovoid. Color: 70D.

*Petals.*—Quantity/arrangement: About five petals in a single whorl. Length: About 2.3 cm. Width: About 1.8 cm. Shape: Obovate. Apex: Rounded. Base: Acute. Margin: Entire. Texture, upper and lower surfaces: Smooth; satiny. Aspect: Slightly cupped. Color: When opening, upper surface: 66A; spots/splotches, brighter than 46A. When opening, lower surface: 77C. Fully opened, upper surface: 67A to 67B, becoming closer to 67C with development; spots/splotches, 46A; at the base, 67D; venation, 67A and 46A, that is, similar to petal color. Fully opened, lower surface: Upper two petals, 57A, lower three petals, 77D; at the base, 155D; venation, 57A.

*Sepals.*—Quantity/arrangement: Five per flower in a single whorl; not imbricate on open flowers. Length: About 1.3 cm. Width: About 3 mm. Shape: Narrowly elliptic. Apex: Acuminate. Margin: Entire. Texture, upper and lower surfaces: Pubescent. Color, upper and lower surfaces: 144A.

*Peduncle* (*umbel stem*).—Length: About 21 cm. Diameter: About 4 mm. Angle: About 30° from vertical. Strength: Strong. Texture: Pubescent. Color: 144A.

*Pedicel* (*individual flower stem*).—Length: About 2.7 cm. Diameter: About 1.5 mm. Angle: Erect to about 90° from vertical. Strength: Strong. Texture: Pubescent. Color: 144A.

*Reproductive organs.*—Androecium: Anther quantity: About five per flower. Anther size: About 1 by 2 mm. Anther shape: Oval. Anther color: 48A. Pollen amount: Scarce. Pollen color: 34A. Gynoecium: Pistil quantity: One per flower. Pistil length: About 8 mm. Stigma shape: Five-parted, star-shaped. Stigma color: 46A. Style length: About 2 mm. Style color: 138C. Ovary color: 138C.

*Seed/fruit.*—Seed and fruit development has not been observed.

Disease/pest resistance: Resistance to pathogens and pests common to *Pelargonium* has not been observed.

It is claimed:

1. A new and distinct cultivar of *Geranium* plant named 'Clips Rosspla', as herein illustrated and described.

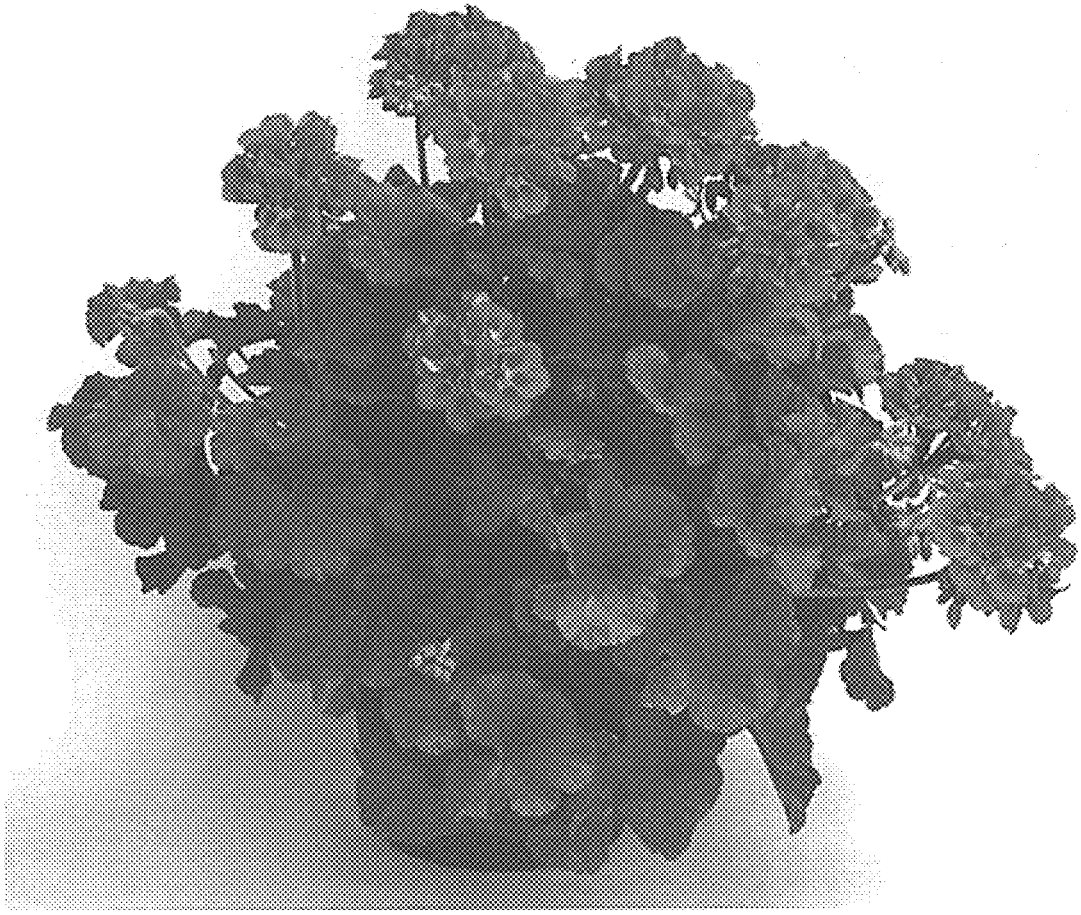
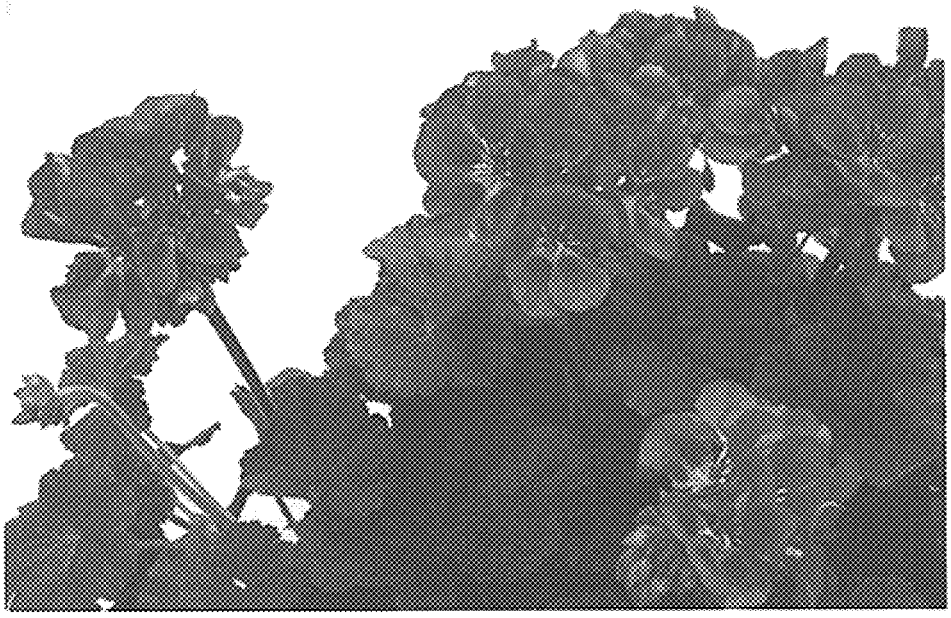

* * * * *